United States Patent [19]
Altwirth

[11] Patent Number: 5,209,777
[45] Date of Patent: May 11, 1993

[54] ADHESIVE AGENT FOR DENTURES OR THE LIKE AND PROCESS FOR THE PRODUCTION THEREOF

[76] Inventor: Oskar Altwirth, Oberach 37, A-4950 Altheim, Austria

[21] Appl. No.: 678,753

[22] Filed: Apr. 1, 1991

Related U.S. Application Data

[63] Continuation of Ser. No. 400,283, Aug. 29, 1989, abandoned.

[51] Int. Cl.$^5$ ............................................. C09K 3/00
[52] U.S. Cl. ...................................... 106/35; 433/180
[58] Field of Search ............................................ 106/35

[56] References Cited

U.S. PATENT DOCUMENTS 3,740,361  6/1973  Altwirth ............................... 106/35
4,315,779  2/1982  Heyd ..................................... 106/35

FOREIGN PATENT DOCUMENTS 229010    7/1987  European Pat. Off. .
2056363  11/1970  Fed. Rep. of Germany .
1287545   8/1972  United Kingdom .

*Primary Examiner*—Mark L. Bell
*Assistant Examiner*—Margaret Einsmann
*Attorney, Agent, or Firm*—Collard & Roe

[57] ABSTRACT

An adhesive agent for dentures consists of a spreadable compound with an alginate, a polyvinyl acetate, a carboxymethyl cellulose and an emulsifier.

In order to obtain a lasting effect, unchanging spreadability and long-term durability, the compound consists of a mixture of a modified mixture of carboxymethyl cellulose and sodium alginate with the polyvinyl acetate, an anionic water- and alcohol-soluble cellulose ether, a gel, a neutral oil and an organically modified montmorillonite as the emulsifier and stabilizer, as well as of an alcohol solvent.

10 Claims, No Drawings

ADHESIVE AGENT FOR DENTURES OR THE LIKE AND PROCESS FOR THE PRODUCTION THEREOF

This is a continuation of copending application Ser. No. 07/400,283 filed on Aug. 29, 1989, now abandoned.

The invention relates to an adhesive agent for dentures or the like consisting of a spreadable compound containing an alginate, a polyvinyl acetate, a carboxymethyl cellulose and an emulsifier, as well as to a process for producing such an adhesive agent.

In order to obtain a spreadable adhesive agent that can be filled in tubes, it has been proposed earlier according to DE-OS 20 56 363 or JP-PS 824 716 of this applicant to mix an alginate with an alcoholic solution of a physiologically harmless solid resin, preferably polyvinyl acetate. This adhesive agent, however, proved to be flawed in practical application in that demulsification of the alginate and polyvinyl acetate occurred shortly after it was tubed, resulting in a loss of efficiency of the adhesive agent. In addition, it was found that the viscosity of the adhesive agent changes due to the loss of alcohol caused by leaking of the tube closures, so that the adhesive agent loses its spreadability. Furthermore, in the course of time, the alginate itself enters into a strong bond with the polyvinyl acetate, which means that the alginate can no longer adequately serve its function of swelling in liquid and absorbing moisture. For enhancing the adhesiveness, it was known, too, to add to the mixture of alginate and polyvinyl acetate carboxymethyl cellulose and a methyl cellulose emulsifier in order to increase the moisture absorption power of the adhesive agent and to retard demulsification of the compound. This adhesive agent in itself stood the test; however, the duration of action of the adhesive agent is still too short and the adhesiveness is unsatisfactory.

Hence the invention is based on the problem of eliminating said drawbacks and to propose an adhesive agent of the type specified above that is characterized by long-term durability, its lasting spreadability, and mainly by its particularly good and durable adhesiveness. In addition, the invention proposes a useful process for the manufacture of said adhesive agent.

Said problem is resolved by the invention in that the compound consists of a mixture of a modified mixture of carboxymethyl cellulose and sodium alginate with the polyvinyl acetate, an anionic water- and alcohol-soluble cellulose ether, preferably hydroxypropyl cellulose, a gel consisting of a neutral oil and an organically modified montmorillonite as the emulsifier and stabilizer, as well as of an alcoholic solvent, preferably ethyl alcohol. Advantageously, the mixture contains 75 constituent parts of the modified mixture of carboxymethyl cellulose and sodium alginate, and 25 constituent parts of the polyvinyl acetate solution including the gel and cellulose ether.

The modified mixture of carboxymethyl cellulose and sodium alginate, because of its highly viscous quality, contributes particularly high liquid absorption power and, in this way, assures a lasting adhesive action. Removal of this mixture by rinsing or flushing is prevented by its incorporation in the polyvinyl acetate, which is softened and becomes sticky by the warmth of the mouth, so that the denture will firmly and lastingly stick to the gum substrate, which is dried by the modified mixture of carboxymethyl cellulose and sodium alginate absorbing the moisture of the mucous membrane. In this connection, adding the cellulose ether permits incorporating this modified mixture of carboxymethyl cellulose and sodium alginate in the alcoholic polyvinyl acetate solution, which heretofore has been very difficult to accomplish. At the same time, the cellulose ether prevents the moisture absorption power of the modified mixture from being impaired by the polyvinyl acetate, so that said modified mixture remains fully absorptive. The cellulose ether effects an intensive surface activity of the entire compound, which reduces the flow of saliva within the cavity of the mouth and increases the durability of the adhesive agent. In addition, the cellulose ether is thermoplastic and acts in the way of a plasticizer, permitting the compound to readily adapt to the mucous membranes. Furthermore, to keep the total compound stable and to assure the required plasticity, a gel consisting of a neutral oil and an organically modified montmorillonite is added to the mixture as a chemically neutral, nontoxic emulsifier and stabilizer. Said gel, furthermore, assures thermal stability of the adhesive agent, such stability being particularly important in view of the temperature variations occurring in the mouth cavity due to eating habits. Another important function of the gel is to neutralize the sensibility of the mucous membranes caused by possible irritation by the alcohol content of the mixture.

For producing the adhesive agent according to the invention, a first mixture is prepared first by dissolving the polyvinyl acetate in the solvent, stirring the cellulose ether into said solution, and adding the gel following a pause and further stirring, whereupon the first mixture and the modified mixture of carboxymethyl cellulose and sodium alginate are admixed and kneaded to obtain a paste-like compound.

For the preparation of the first mixture, 4 constituent parts of a hydroxypropyl cellulose are stirred into a solution consisting of 68 constituent parts of a polyvinyl acetate solid resin and 32 constituent parts of an 85% ethyl alcohol. Thereafter, the solution is stored for at least 48 hours with exclusion of air, whereupon 6 constituent parts of the gel is admixed preferably at a temperature of 30° C. The modified mixture is prepared by completely dissolving equal constituent parts of carboxymethyl cellulose and sodium alginate in water, subsequently thickening said solution in vacuum to a pulpy mass, drying via steam-heated drying rolls, and pulverizing. Subsequently, 25 constituent parts of the first solution and 75 constituent parts of the modified mixture are admixed for completing the manufacture of the adhesive compound, whereby intensive agitation and gradual admixing are important. The finished compound is then loaded in a separate kneader and kneaded until a homogeneous, paste-like compound is obtained, which then has to be filled only in tubes. Such tubing is facilitated by heating the compound to about 30° C.

I claim:

1. An adhesive agent for dentures consisting of a spreadable compound of
   (a) 75 parts of a mixture of carboxymethyl cellulose and sodium alginate, and
   (b) 25 parts of an alcoholic solution of polyvinyl acetate containing an anionic water- and alcohol-soluble cellulose ether and an emulsifying and stabilizing gel comprised of a neutral oil and an organically modified montmorillonite.

2. The adhesive agent of claim 1, wherein the mixture of (a) contains equal parts of carboxymethyl cellulose and sodium alginate.

3. The adhesive agent of claim 1, wherein the cellulose ether is hydroxypropyl cellulose.

4. The adhesive agent of claim 3, wherein the alcoholic solution of (b) contains 68 parts of polyvinyl acetate, 32 parts of 85% ethyl alcohol, 4 parts of hydroxypropyl cellulose and 6 parts of the gel.

5. A process of producing an adhesive agent for dentures consisting of a spreadable compound, which comprises the steps of
   (a) preparing a solution of polyvinyl acetate in an alcoholic solvent, stirring an anionic water- and alcohol-soluble cellulose ether into the alcoholic polyvinyl acetate solution, storing the resultant solution and finally stirring an emulsifier and stabilizer gel comprised of a neutral oil and an organically modified montmorillonite into the stored solution to obtain a first mixture,
   (b) mixing 75 parts of a mixture of carboxymethyl cellulose and sodium alginate with 25 parts of the first mixture, and
   (c) kneading the mixtures until a paste-like, spreadable compound is obtained.

6. The process of claim 5, wherein equal parts of carboxymethyl cellulose and sodium alginate are mixed to obtain the mixture of (b).

7. The process of claim 6, wherein the carboxymethyl cellulose and the sodium alginate of (b) are dissolved in water, the resultant solution is thickened under vacuum until a pulpy compound is obtained, the pulpy compound is dried and the dried compound is pulverized.

8. The process of claim 5, wherein the cellulose ether is hydroxypropyl cellulose.

9. The process of claim 8, wherein 68 parts of polyvinyl acetate, 32 parts of 85% ethyl alcohol, 4 parts of hydroxypropyl cellulose and 6 parts of the gel are mixed to obtain the first mixture.

10. The process of claim 5, wherein the resultant solution of (a) is anaerobically stored for at least 48 hours and the gel is stirred in at a temperature of 30° C.

* * * * *